US00PP35000P2

(12) United States Plant Patent
Scheys

(10) Patent No.: US PP35,000 P2
(45) Date of Patent: Feb. 21, 2023

(54) ***HEUCHERA* PLANT NAMED 'PINKY PANKY'**

(50) Latin Name: ***Heuchera* hybrid**
Varietal Denomination: 'Pinky Panky'

(71) Applicant: Diederik Alexander Maria Scheys, Torcé-Viviers en Chamie (FR)

(72) Inventor: Diederik Alexander Maria Scheys, Torcé-Viviers en Chamie (FR)

( * ) Notice: Subject to any disclaimer, the term of this patent is extended or adjusted under 35 U.S.C. 154(b) by 0 days.

(21) Appl. No.: 17/858,649

(22) Filed: Jul. 6, 2022

Related U.S. Application Data

(60) Provisional application No. 63/318,018, filed on Mar. 9, 2022.

(51) Int. Cl.
*A01H 5/02* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Heuchera* a plant named 'Pinky Panky' that is characterized by its leaves that are white in color, finely mottled and edged green, with pink veins and surfaces that are flushed with pink and its flowers that are pink in color.

2 Drawing Sheets

Botanical classification: *Heuchera* hybrid.
Cultivar designation: 'Pinky Panky'.

BACKGROUND OF THE INVENTION

The present invention relates to a new and distinct cultivar of *Heuchera* of hybrid origin, botanically known as *Heuchera* 'Pinky Panky' and is hereinafter referred to by its cultivar name 'Pinky Panky'.

The new cultivar originated as a seedling that arose from seed planted from open pollination of an unnamed and unpatented plant of *Heuchera* from the Inventor's breeding program in Réty, France. The male parent of 'Pinky Panky' is therefore unknown. 'Pinky Panky' was selected as a single unique plant in spring of 2017 from the resulting seedlings.

Asexual propagation of the new cultivar was first accomplished under the direction of the Inventor by tissue culture initiated from meristem tissue in September of 2019 in Lochristi, Belgium. Asexual propagation of the new cultivar by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Pinky Panky' as a new and unique cultivar of *Heuchera*.

1. 'Pinky Panky' exhibits leaves that are white in color, finely mottled and edged green, with pink veins and surfaces that are flushed with pink.
2. 'Pinky Panky' exhibits flowers that are pink in color.

The female parent plant of 'Pinky Panky' is similar to 'Pinky Panky' in having white and green mottled foliage but differs from 'Pinky Panky' in lacking foliage with pink veins and flushed pink coloration. 'Pinky Panky' can be most closely compared to the *Heuchera* cultivars 'Snowfire' (not patented) and 'Snow Angel' (not patented). 'Snowfire' is similar to 'Pinky Panky' in having leaf veins that are pink in color. 'Snowfire' differs from 'Pinky Panky' in having pink coloration only in the leaf veins and foliage that has large white spots and splashes. 'Snow Angel' is similar to 'Pinky Panky' in having foliage with green and white coloration. 'Snow Angel' differs from 'Pinky Panky' in having foliage that is rarely flushed with pink and in having large white spots and splashes.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Le Jardin du Chat Vert (blog), RHS Chelsea show, Spanne Plantsalg, Sunds, Hortweek, Plant Estate, Fleur, Maytree Nursery, Deux Caps, Border in a Box, Clematis Nursery Co., Promesse de fleurs, Heucheraholics, The Biking Gardener, Hedging Co., Shoot Gardening, Cool Plants, and Twigs Nurseries.

BRIEF DESCRIPTION OF THE DRAWINGS

The accompanying color photographs illustrate the overall appearance and distinct characteristics of the new *Heuchera*.

The photograph in FIG. 1 was taken of a plant 2 years in age as field grown outdoors in Rety, France and provides a close-up view of the foliage of 'Pinky Panky'.

Figure 1:
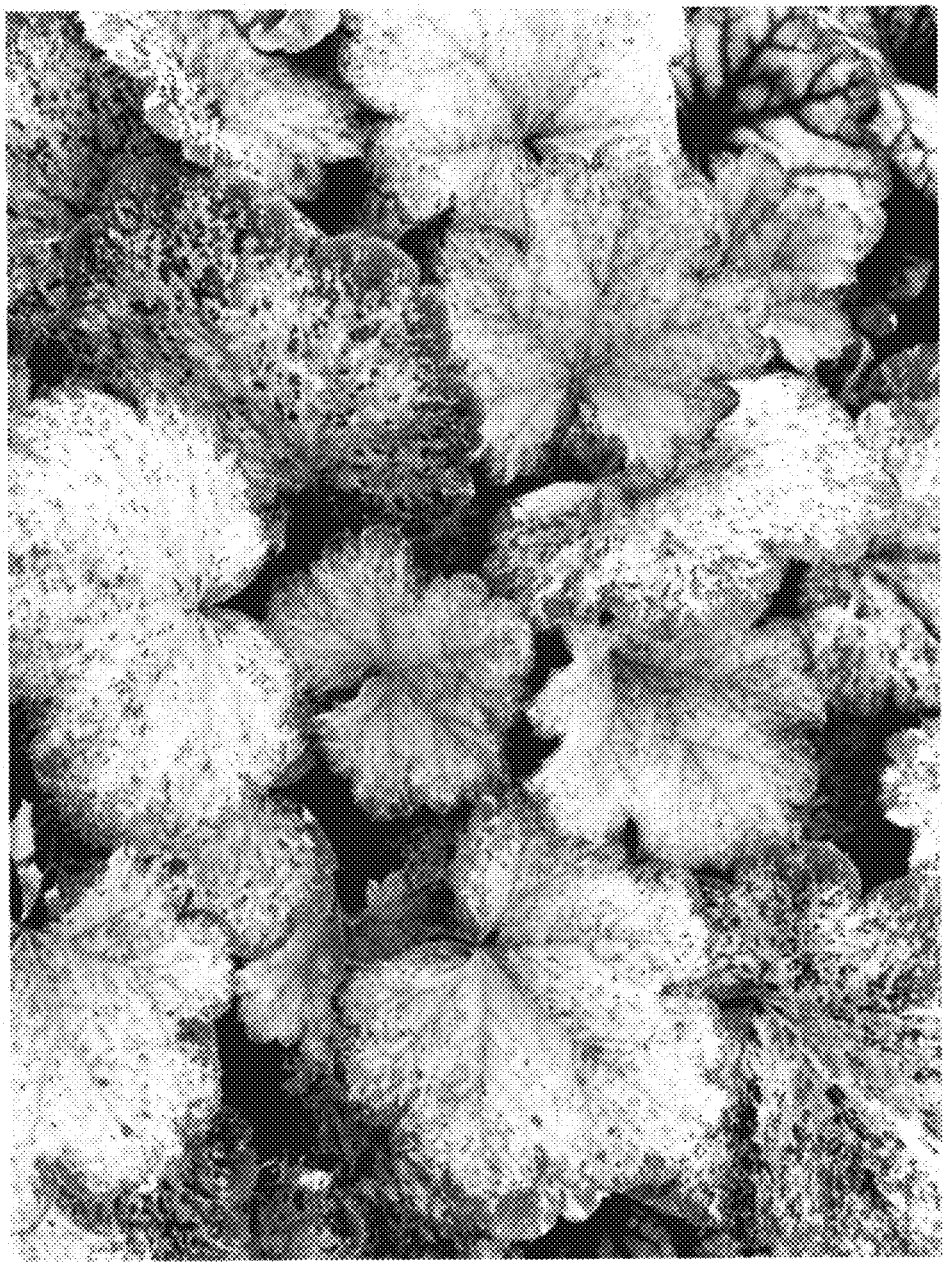
Figure 2:
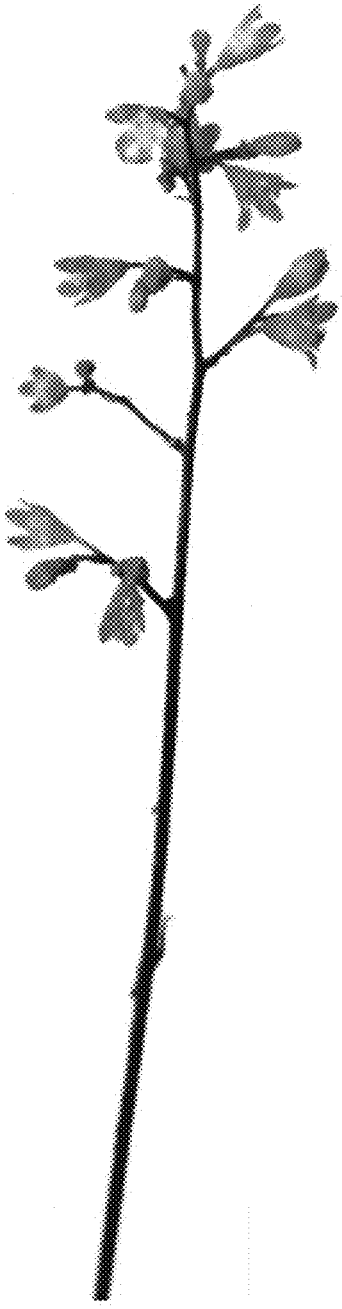

The photograph in FIG. 2 was taken of a plant 10 months in age as grown outdoors in a 9-cm container in Torcé Viviers en Charnie, France and provides a close-up view of an inflorescence of 'Pinky Panky'.

The colors in the photograph are as close as possible with the digital photography techniques available, the color values cited in the detailed botanical description accurately describe the colors of the new *Heuchera*.

DETAILED BOTANICAL DESCRIPTION OF THE PLANT

The following is a detailed description of plants 10 months in age as grown outdoors in 9-cm containers in Torcé Viviers en Charnie, France. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—April and May in France.

*Plant type.*—Herbaceous perennial.

*Plant habit.*—Flattened globular with inflorescences held above the foliage.

*Height and spread.*—An average of 15 cm in height (soil level to top of foliar plane), average of 55 cm in height (soil level to top of floral plane) and 30 cm in spread.

*Hardiness.*—At least in U.S.D.A. Zones 4 to 9.

*Diseases and pests.*—No susceptibility or resistance to pests or diseases has been observed.

*Root description.*—Fibrous roots on woody rootstalks.

*Propagation.*—Tissue culture.

*Root development.*—An average of 3 weeks for root initiation, 6 weeks to produce a rooted cutting.

*Growth rate.*—Slow.

Stem description; None present, leaves emerge as basal rosettes from roots.

Foliage description:

*Leaf shape.*—Reniform to broad ovate in outline.

*Leaf division.*—Simple.

*Leaf base.*—Hastate, lobes touching to very slightly overlapping.

*Leaf apex.*—Obtuse to very short and abruptly acute.

*Leaf venation.*—Laciniate, upper surface matches leaf surface, lower surface N148C.

*Leaf margins.*—Crenate, each lobe has an obtuse to very short abruptly acute tip, moderately undulate and moderately covered with very short hairs, average of 0.4 mm in length, N155A in color.

*Leaf attachment.*—Petiolate.

*Leaf arrangement.*—Alternate in basal rosettes.

*Leaf lobes.*—Lobed, an average of 5 to 7 lobes, shallow in depth, divergent, lobe margins free.

*Leaf surface.*—Both surfaces non-rugose, smooth and pubescent, moderately covered with very short strigose hairs an average of 0.2 mm in length and too small to measure color.

*Leaf color.*—Young upper surface; a blend of N186C and N200A and slightly lighter, strongly and irregularly marbled and blotched 51B, young lower surface; a blend of N186C and 187A and slightly lighter, strongly irregularly marbled and blotched 51A, mature upper surface; 197A and slightly darker, strongly irregularly dotted, marbled and blotched 147A and 51C to 51D and lighter, mature lower surface; a blend of 59B and 187D, moderately irregularly dotted, marbled and blotched 51B to 51C.

*Leaf size.*—An average of 4.2 cm in length and 4.4 cm in width.

*Leaf quantity.*—An average of 8 per basal rosette.

*Petioles.*—An average of 9.4 cm in length and 1 mm in diameter, medium strength, both surfaces slightly glossy, upper surface color 178B, tinged 184B to 184C, lower surface color 152B.

*Stipules.*—Leafy stipules at the base of each leaf, average of 1 cm in length, average of 0.3 cm in width, tip acute, pointing outward in an average angle 70° to peduncle, 153D in color and base 54C at base.

Flower description:

*Inflorescence type.*—Numerous small bell-shaped flowers arranged on panicles on peduncles emerging from a basal rosette.

*Inflorescence size.*—An average of 6.9 cm in height and 3.8 cm in diameter.

*Inflorescence number.*—An average of 3.

*Flower fragrance.*—None.

*Flower quantity.*—Average of 27 flowers per inflorescence, 50 flowers per plant, 150 buds and flowers per plant.

*Flower lastingness.*—Average of one week.

*Flower buds.*—Obovate in shape, an average of 4 mm in length and 2.5 mm in diameter, color; 54C, top 50B, lower half 54A, surface is matte and moderately covered with very short glandular hairs; an average of 0.2 mm in length and too small to measure color.

*Flower aspect.*—Outward to slightly nodding.

*Flower type.*—Single, campanulate.

*Flower size.*—Average of 8 mm in height, diameter, and length.

*Petals.*—Average of 5, oblanceolate in shape, margin is entire, apex is acute, base is acuminate, upper and lower surface is glabrous, smooth and matte, an average of 3 mm in length and 1 mm in width, color when opening upper surface; N155B, base 65B to 65C, color when opening lower surface; N155B, base 65A, fully open upper surface; N155B, base 65C, fully open lower surface; N155B, base 65A to 65B.

*Calyx.*—Campanulate, sepals fused to hypanthium, 8 mm in length and diameter.

*Sepals.*—An average of 5, lower 62.5% fused into campanulate hypanthium, free part ovate in shape, an average of 8 mm in length and 0.3 mm in width, margin is entire and fused into hypanthium, apex is acute, color; when opening upper surface; lower half 55C, upper half 54A to 54B, when opening lower surface; 54C, top 50B, lower half 54A, fully open upper surface; 55C, upper half 54B, fully open lower surface; 54C, top 51A, lower half 54A, surface is smooth and covered with very short glandular hairs, average of 0.2 mm in length and to small to measure color.

*Peduncle.*—An average of 31.2 cm in length and 2 mm in diameter, 176A and 178A in color, primary flower aspect 70° to horizontal, secondary peduncle aspect to main peduncle 50°, moderate in strength, surface moderately glossy and moderately covered with very short soft glandular hairs; average of 0.5 mm in length, N155A in color.

*Pedicels.*—An average of 2.5 mm in length and 0.5 mm in diameter, 182A in color, primary flower aspect straight on top of secondary pedicel, secondary and tertiary flower aspect is 30°, moderate in strength, surface matte and moderately covered with very short soft glandular hairs; average of 0.2 mm in length and too small to measure color.

Reproductive organs:

*Gynoecium.*—Pistils; 2, 3 mm in length, stigma; club-shaped, too small to measure color, 0.2 mm in diameter, style; an average of 2.75 mm in length, color; NN155B, base 157D, ovary; 54A in color.

*Androecium.*—Stamens; 5, anthers; ovate in shape, average of 0.5 mm in length and width, 22A in color, filament; 3 mm in length and NN155D in color, pollen; moderate in quantity and 24A in color.

*Seed/fruit.*—No fruit or seeds were observed to date.

It is claimed:

1. A new and distinct cultivar of *Heuchera* plant named 'Pinky Panky' as herein illustrated and described.

* * * * *